United States Patent
Linker (10) Patent No.: US 8,561,483 B1
(45) Date of Patent: Oct. 22, 2013

(54) PRECONCENTRATOR WITH HIGH VOLUME CHILLER FOR HIGH VAPOR PRESSURE PARTICLE DETECTION

(75) Inventor: Kevin L. Linker, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 391 days.

(21) Appl. No.: 13/094,615

(22) Filed: Apr. 26, 2011

(51) Int. Cl.
*G01N 1/22* (2006.01)

(52) U.S. Cl.
USPC ................................ 73/863.12

(58) Field of Classification Search
USPC ................................ 73/863.12
See application file for complete search history.

(56) References Cited

U.S. PATENT DOCUMENTS

| | | | |
|---|---|---|---|
| 5,457,720 A * | 10/1995 | Snyder et al. | 376/253 |
| 5,854,431 A | 12/1998 | Linker et al. | |
| 5,939,831 A * | 8/1999 | Fong et al. | 315/111.21 |
| 6,345,545 B1 | 2/2002 | Linker et al. | |
| 7,299,711 B1 | 11/2007 | Linker et al. | |
| 2010/0298738 A1 * | 11/2010 | Felts et al. | 600/576 |

OTHER PUBLICATIONS

Large-Volume Sampling and Preconcentration, 3$^{rd}$ Explosives Detection Technology Symposium and Aviation Security Technology Conference, Atlantic City, NJ, Nov. 26-27, 2001 by Kevin L. Linker, 10 pages.

* cited by examiner

*Primary Examiner* — Hezron E Williams
*Assistant Examiner* — Rodney T Frank
(74) *Attorney, Agent, or Firm* — Daniel J. Jenkins (57) ABSTRACT

Apparatus and method for collecting particles of both high and low vapor pressure target materials entrained in a large volume sample gas stream. Large volume active cooling provides a cold air supply which is mixed with the sample gas stream to reduce the vapor pressure of the particles. In embodiments, a chiller cools air from ambient conditions to 0-15° C. with the volumetric flow rate of the cold air supply being at least equal to the volumetric flow rate of the sample gas stream. In further embodiments an adsorption media is heated in at least two stages, a first of which is below a threshold temperature at which decomposition products of the high vapor pressure particle are generated.

20 Claims, 7 Drawing Sheets

PRECONCENTRATOR WITH HIGH VOLUME CHILLER FOR HIGH VAPOR PRESSURE PARTICLE DETECTION

GOVERNMENT INTERESTS

Embodiments of the invention were developed under Contract No. DE-AC04-94AL85000 between Sandia Corporation and the U.S. Department of Energy. The United States Government has certain rights in this invention.

TECHNICAL FIELD

Embodiments of the invention are in the field of particle detection and more particularly relate to detection of high vapor pressure particulates present in a high volume gas stream.

BACKGROUND

Trace chemical detection of explosives, i.e., the art of detecting explosive materials from minute quantities of vapor and/or microscopic particles (hereinafter referred to as "particles"), can be an important aspect of many physical security and contraband detection systems. In many applications, especially applications involving the general public such as airport passenger screening, swipe collection of particles via direct physical contact with the person or object to be screened for explosives is either too physically invasive or time consuming, so it is advantageous to base the collection process on air flows. But the particle material that is collected in such air flows is usually far more dilute than the detector is capable of measuring, and the air flow is often too large to be directly accommodated by the detector. These disparities give rise to preconcentrators, devices which take a trace sample of a material from a large incoming air flow and concentrate the material into a smaller volume before it is introduced into a trace detector.

U.S. Pat. Nos. 5,854,431 and 6,345,545 disclose single stage and multi-staged preconcentrators, respectively, for use in collecting particles from an air stream that passes over a person or object under observation. While these preconcentrators concentrate particles in a high volume gas flow for detection in a low volume gas flow, they are best suited to low vapor pressure (LVP) explosive detection. Recently however, high vapor pressure (HVP) explosives have come into more common use such that both LVP and HVP explosive detection is needed. A means to collect and preconcentrate HVP explosives is therefore desirable.

SUMMARY OF THE DESCRIPTION

Apparatus and methods for collecting particles of both HVP and LVP target materials entrained in a large volume sample gas stream are described herein. A cold air supply is provided through large volume active cooling. The cold air supply is mixed with the sample gas stream to reduce the vapor pressure of the particles.

Figure 1:
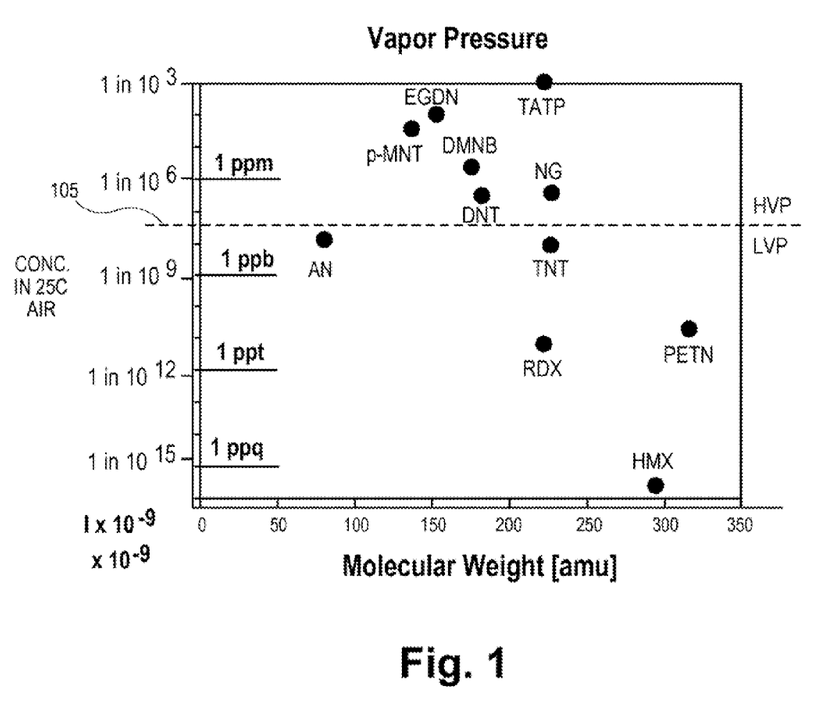

In one embodiment, an apparatus for collecting particles entrained in a sample gas stream includes a first duct to conduct a coolant gas stream at a first volumetric flow rate and a second duct to conduct the sample gas stream at a second volumetric flow rate. A chiller is coupled to the first duct to cool the coolant gas stream to a temperature below that of the sample gas stream. In embodiments, the chiller cools air from ambient conditions to 0-15° C. with the volumetric flow rate of the cold air supply being at least equal to the volumetric flow rate of the sample gas stream.

An adsorption media in fluid communication with each of the sample gas stream and the coolant gas stream concurrently is to collect the particles entrained in the sample gas stream at a temperature below that of the sample gas stream, the adsorption media is further to be in alternate fluid communication with a third duct to transfer the particles from the adsorption media to a carrier gas stream having a third volumetric flow rate toward a downstream particle detector, the third volumetric flow rate being lower than the second volumetric flow rate. In further embodiments an adsorption media is heated in at least two stages, a first of which is below a threshold temperature at which decomposition products of the HVP particle are generated.

BRIEF DESCRIPTION OF THE DRAWINGS

Embodiments of the present invention are illustrated by way of example, and not limitation, in the figures of the accompanying drawings in which:

FIG. 1 is a graph of vapor pressures for a subset of common LVP and HVP explosives;

FIG. 2 is a schematic of an apparatus for collecting particles entrained in a sample gas stream, the apparatus incorporating a high volume chiller, in accordance with an embodiment;

FIG. 3 is a flow diagram illustrating operation of the apparatus depicted in FIG. 2, in accordance with an embodiment;

FIG. 4 illustrates a schematic of an apparatus for collecting particles entrained in a sample gas stream, the apparatus incorporating a high volume chiller and an adsorption media heater, in accordance with an embodiment;

FIG. 5 is a graph of adsorption media temperature over time for a staged transfer of HVP and LVP particles into a carrier gas, in accordance with an embodiment;

FIG. 6 is a flow diagram illustrating staged adsorption media heating, in accordance with an embodiment;

FIG. 7 illustrates a schematic of an apparatus for collecting particles entrained in a sample gas stream, the apparatus incorporating a high volume chiller and multi-staged preconcentrators, in accordance with an embodiment; and FIG. 8 is a flow diagram illustrating operation of the apparatus depicted in FIG. 7, in accordance with an embodiment.

DETAILED DESCRIPTION

In the following description, numerous details are set forth. It will be apparent, however, to one skilled in the art, that the present invention may be practiced without these specific details. In some instances, well-known methods and devices are shown in block diagram form, rather than in detail, to avoid obscuring the present invention. Reference throughout this specification to "an embodiment" means that a particular feature, structure, function, or characteristic described in connection with the embodiment is included in at least one embodiment of the invention. Thus, the appearances of the phrase "in an embodiment" in various places throughout this specification are not necessarily referring to the same embodiment of the invention. Furthermore, the particular features, structures, functions, or characteristics may be combined in any suitable manner in one or more embodiments. For example, a first embodiment may be combined with a second embodiment anywhere the two embodiments are not mutually exclusive.

Generally, HVP materials targeted for detection have vapor pressures of at least parts per billion (ppb) to parts to thousand. At these vapor pressures the material exits only as a vapor. FIG. 1 shows a vapor pressure chart for certain common explosive compounds (triacetone triperoxide (TATP), ethylene glycol dinitrate (EGDN), para-mononitrotoluene (p-MNT), 2,3-dimethyl-2,3-dinitrobutane (DMNB), nitroglycerin (NG), dinitrotoluene (DNT), ammonium nitrate (AN), trinitrotoluene (TNT), pentaerythritol (PETN), cyclotrimethylenetrinitramine (RDX), and octogen (HMX)) grouped into high and low vapor pressure classes. On the y-axis is the saturated equilibrium concentration in air at 25° C. for the depicted explosive compounds. On the x-axis is the molecular weight, in amu, for the depicted explosive compounds. As demarked by 105 on FIG. 1, TATP, EGDN, p-MNT, DMNB, NG, DNT are classified herein as HVP explosives while AN, TNT, PETN, RDX, and HMX are classified as LVP explosives.

Figure 2:
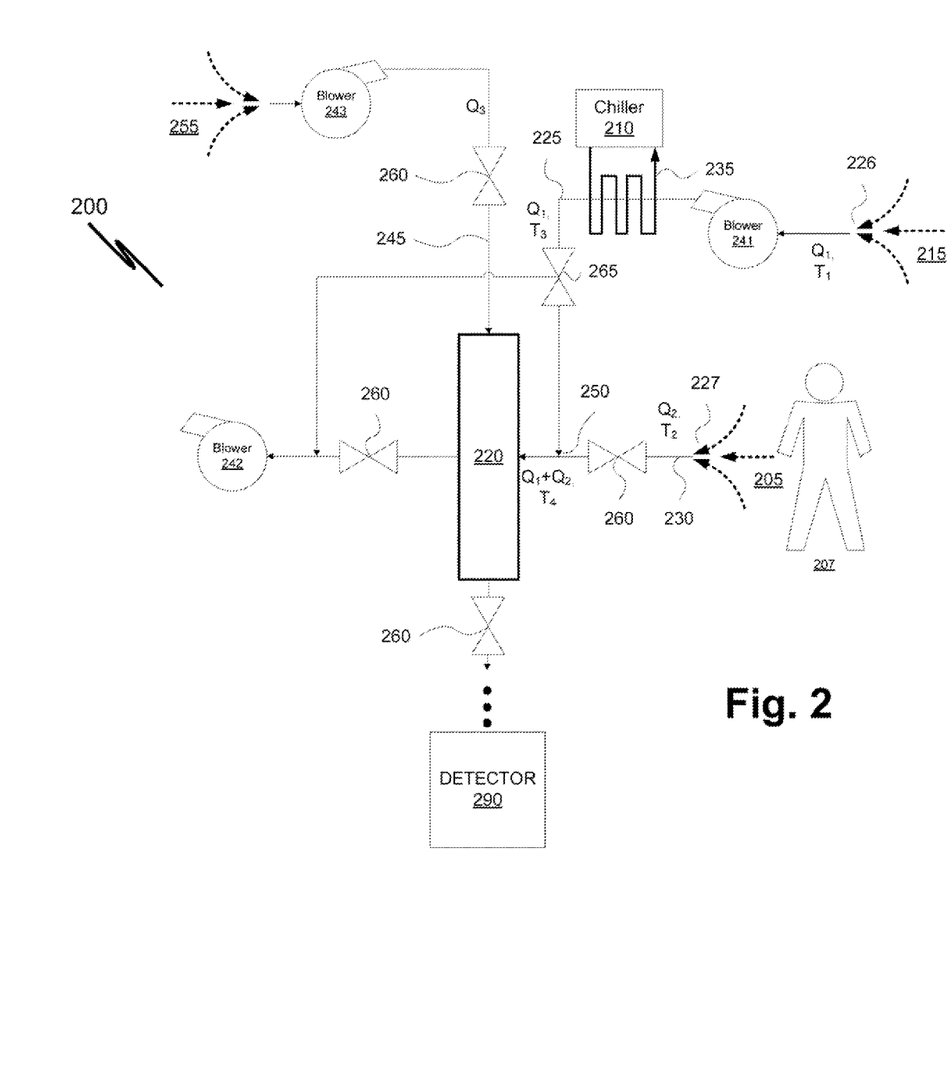

FIG. 2 is a schematic of an apparatus 200 for collecting particles entrained in a sample gas stream 205 associated with a source 207. The apparatus 200 includes a chiller 210 which is to provide coolant gas stream 215 for mixing with the sample gas stream 205. The sample gas stream 205 temperature is to be cooled by the coolant gas and the vapor pressure of the particles present in the sample gas stream 205 thereby reduced. Generally, vapor pressures of the HVP materials, such as the HVP explosives depicted in FIG. 1, are approximately halved for every 5° C. reduction in temperature. With a reduce vapor pressure, the particles associated with HVP materials, such as the HVP explosives depicted in FIG. 1, can be made to collect on an adsorption media 220.

While the coolant gas stream may generally comprise any gas, in an embodiment, the coolant gas stream 215 is made up of air taken in at a cold air supply intake 226. The cold air supply intake 226 is preferably disposed a sufficient distance away from the source 207 so that the coolant gas stream is free of particulates targeted for detection by the apparatus 200. Collection of targeted particles at the cold air supply intake 226 is to be avoided to prevent adsorption of such particles onto the chiller's heat transfer surfaces 235 which would then risk cross-contamination of the adsorption media 220 between successive sources 207. At the cold air supply intake 226, air may be at ambient conditions such that for embodiments where the apparatus 200 is in climate controlled environments, the air is at a first temperature, $T_1$, which is approximately 25° C. while relative humidity of the air is between about 20% and about 80%. In certain embodiments, the air may be filtered at the intake 226 and may also be dehumidified. In particular embodiments, clean dry air (CDA) is sourced at the intake 226. In alternative embodiments, the apparatus 200 includes a closed loop cold air supply such that intake 226 is coupled to a point in the cold air supply ducting downstream of the adsorption media 220 for a cold air supply that is at least partially recirculated (not depicted).

As further illustrated in FIG. 2, a first duct 225 is configured to conduct intake air across the chiller's heat transfer surfaces 235 at a first volumetric flow rate, $Q_1$, induced by a first impeller, such as blower 241. A second duct 230 is configured to conduct the sample gas stream 205, having a second volumetric flow rate, $Q_2$, induced by a second impeller, such as blower 242. The second duct 230 is in parallel with the first duct 225 upstream of the adsorption media 220 with the chiller 210 upstream of a union 250 joining the first and second ducts, 225 and 230 which is upstream or coincident with the adsorption media 220. The second duct 230 bypasses the heat transfer surfaces 235 en route to the adsorption media 220 to avoid particle adsorption on surfaces other than the adsorption media 220.

In embodiments, the sample gas stream 205 has a large volumetric flow rate $Q_2$, ranging from at least 1 liter/second to 1000 liters/sec, or more. The large $Q_2$ is to accommodate sample collection from a large surface area source 207, such as a parcel, luggage, a person, an automobile, a shipping container, etc. In the exemplary embodiment where the source 207 is a person, $Q_2$ is at least 50 liters/sec and often 100 to 200 liters/sec. The sample gas stream 205 is typically at ambient conditions (standard pressure and temperature) with a relative humidity ranging from about 10% to about 90%, or more, where the apparatus 200 is operated out of doors and from about 20% to about 80% where the apparatus is operated in climate controlled environments.

In embodiments, the coolant gas stream is conducted through the first duct 225 at a volumetric flow rate, $Q_1$ which is on the same order as the volumetric flow rate of the sample gas stream 205($Q_2$). $Q_1$ is to be comparable to $Q_2$ particularly for embodiments where the air is at ambient conditions and subject to fluctuations in moisture content. In an embodiment, $Q_1$ is at least equal to $Q_2$ and in further embodiments may be between 1 and 3 times $Q_2$ as a function of ambient conditions, particularly moisture content at the air intake 226. Hence, $Q_1$ may range from 1 to 3000 liters/second, is preferably at least 50 liters/second, and is in the 100-300 liters/second range for an exemplary embodiment where the system 200 is disposed in a climate controlled environment (i.e., conditioned ambient air) and configured for collecting a sample from a human.

The chiller 210 is coupled to the first duct 225 and configured for cooling the large coolant gas stream volumetric flows described herein to a temperature, $T_3$, which is below the sample gas stream temperature $T_2$. In an embodiment the chiller 210 comprises any refrigeration means known in the art to be suitable for the volumetric flows, $Q_1$. Vortex tubes, and other means known in the art similarly adaptable only to relatively lower volumetric flows, are not well suited for the cooling the large volumetric flows of $Q_1$ describe herein. As such, an active refrigeration means is preferred. In the exemplary embodiment, the chiller 210 cycles a refrigerant through compressed and expanded states, with the heat transfer surfaces 235 cooled by the refrigerant. In a particular embodiment, the heat transfer surfaces 235 comprise a heat exchanger, such as an air coil with the refrigerant on a liquid side and the coolant gas on an air side. In the exemplary embodiment, the chiller 210 is has a thermal rating sufficient to cool the coolant gas stream by at least 5° C. relative to in intake temperature $T_1$ to approximately halve vapor pressures of the exemplary particles targeted for detection. In advantageous embodiments, the chiller 210 is has a thermal rating sufficient to cool the coolant gas stream by at least 10° C. relative to in intake temperature $T_1$. In exemplary in-door embodiments, where a cold air supply intakes ambient air from a conditioned environment at an intake temperature $T_1$ of about 25° C., the chiller 210 is has a thermal rating sufficient to provide a cold air supply temperature $T_3$ of between about 0° C. and about 20° C., with $T_3$ in the exemplary embodiment being between about 5° C. and about 15° C. for a $T_1$ of about 25° C.

At the union 250 the first and second ducts 225 and 230 join. The union 250 may be upstream or coincident with the adsorption media 220. The union 250 may, for example comprises a T-fitting or Y-fitting. Any flow modifier may be adapted to the union 250 or in ducting between the union 250 and adsorption media 220 to improve Mixing of the sample gas stream 205 with the coolant gas stream 215. For example, laminar flow achieved in the second duct 230 for the sake of limiting deposition of particles on duct surfaces may be disrupted downstream of the union 250 for the sake of mixing the sample gas stream 205 with the coolant gas stream 215 to achieve the most significant vapor pressure reduction. In certain embodiments, the union 250 is disposed a distance upstream of the adsorption media 220 to provide a residence time, τ, between the union 250 and the adsorption media 220 sufficient to reduce the sample gas stream 205 temperature $T_2$ by at least 5° C. and thereby reduce target material vapor pressures by approximately half.

As illustrated, the adsorption media 220 is to be in fluid communication with each of the sample gas stream 205 and the coolant gas stream 215. The adsorption media 220 is to collect particles entrained in the sample gas stream 205 at a temperature, $T_4$, which is below that of the sample gas stream ($T_2$). The temperature $T_4$ is a function of the mass and energy balance between the sample gas stream 205 and the coolant gas stream concurrently introduced to the adsorption media 220 and is therefore subject to a variety of design choices. In the simplest case, where $Q_1$ is approximately equal to $Q_2$, and the heat capacity of the respective streams is also approximately equal, $T_4$ will approximately average $T_2$ and $T_3$. Thus, were $Q_1$ is approximately equal to $Q_2$ with $Q_1$ comprising cold air at 15° C. and $Q_2$ comprising ambient air at 25° C., T4 will be approximately 20° C. with a volumetric flow rate, $Q_4$, of $Q_1+Q_2$ (e.g., 2 liters/sec-4000 liters/sec with the exemplary flow rate of approximately 400 liters/sec).

The adsorption media 220 may be any known in the art capable of conducting the volumetric flow, $Q_4$ with a pressure drop sustainable by the blowers 241 and 242 and further capable of collecting targeted particles entrained in the sample gas stream 205. In an embodiment, the adsorption media 220 is "porous mesh" defined herein to include other forms of porous structures, in addition to a mesh structure, including a metallic filter, a felt or felt-like mat of finely-drawn wires, a woven screen of metal wires, a porous foamed metal structure, a microporous metallic filter with micro-holes, and a felt-like mat of sintered metal wires. In particular embodiments, any of the materials described in U.S. Pat. No. 5,854,431 may be utilized as the adsorption media 220. In further embodiments, the adsorption media 220 further includes organic and/or polymeric materials coated on a mesh substrate.

As further depicted in FIG. 2, a third duct 245 is configured conduct a carrier gas stream 255 toward a downstream particle detector 290 at a third volumetric flow rate, $Q_3$. A third impeller, such as blower 241, induces $Q_3$ to be considerably lower than the second volumetric flow rate for purposes of preconcentration of both the HVP and LVP particles as they are subsequently desorbed from the adsorption media 220. The apparatus 200 includes flow diverters 260 coupled to the second and third ducts to alternately place the adsorption media in fluid communication with either of the second and third ducts to alternately transfer particles to the adsorption media 220 from the sample gas stream 205 and then transfer the particles from the adsorption media 220 to the carrier gas stream 255. The carrier gas stream 255 then transports the particles toward a chemical detector 290, such as, but not limited to, an ion mobility spectrometer (IMS) or mass spectrometer (MS). As implementation details pertaining to the flow diverters 260, carrier gas stream 255, and chemical detector 290 may all be found in U.S. Pat. No. 5,854,431, no further description of these components is provided herein.

In the exemplary embodiment illustrated in FIG. 2, the apparatus 200 includes a bypass 265 upstream of the adsorption media 220. The bypass 265 functions to maintain a thermal load on the chiller 210 even when the sample gas stream 205 or adsorption media 220 are not coupled with the coolant gas stream 205. Absent the ability to control the thermal load on the chiller 210, the heat transfer surfaces 235 may ice over. The bypass 265 is operable in a first position to conduct the coolant stream through the first duct 225 toward the adsorption media 220 when the sample gas stream 205 is in fluid communication with the adsorption media 220. The bypass 265 is further operable in a second position to isolate the coolant stream 215 from the adsorption media 220 when the carrier gas stream 255 is in fluid communication with the adsorption media 220.

Figure 4:
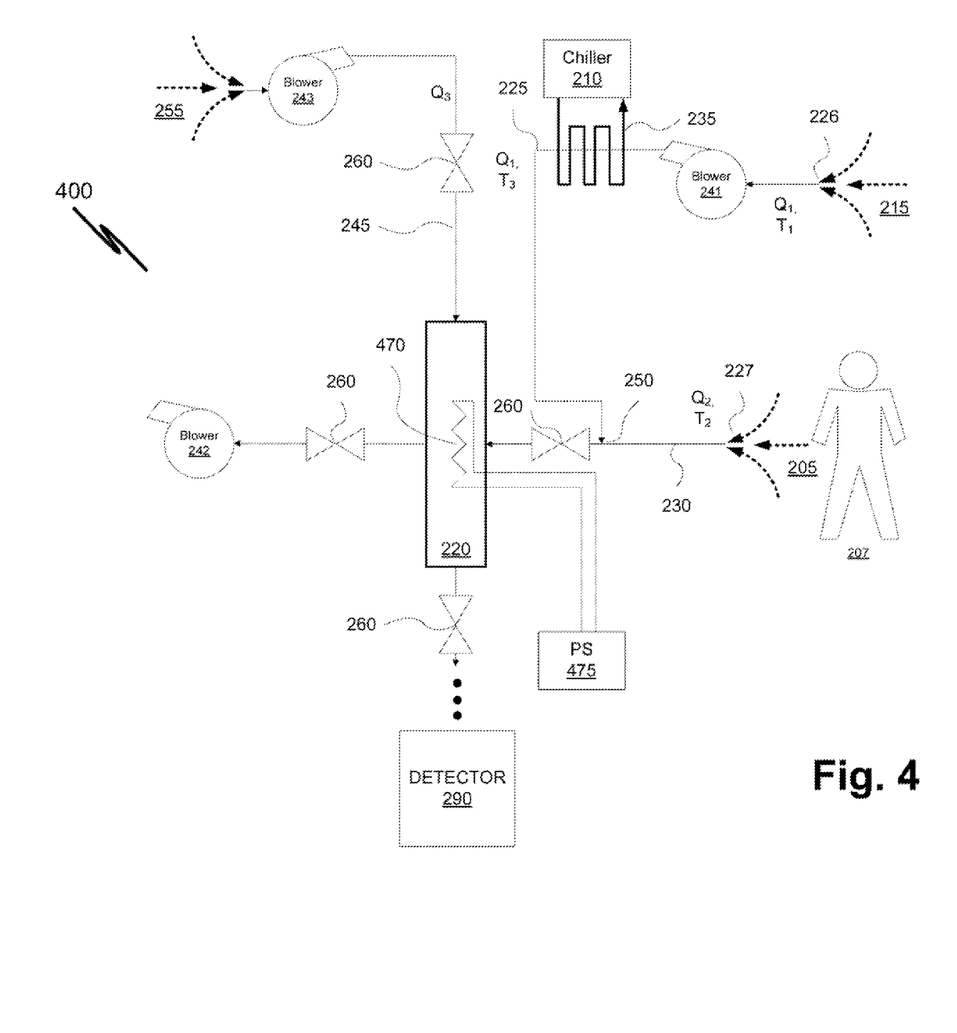

In a first embodiment where the union 250 is downstream of the flow diverter 260 coupled to the second duct 230 (e.g., as depicted in FIG. 2), the bypass 265 may be a flow diverter which is controlled in concert with the flow diverters 260 to couple the coolant gas stream with the blower 242 downstream of the adsorption media 220. In an alternate embodiment, where the union 250 is upstream or coincident with the flow diverter 260 coupled to the second duct 230 (e.g., as depicted in FIG. 4), the bypass 265 may further be incorporated into, or upstream of, the flow diverter 260 such that in a first position both the sample gas stream 205 and the coolant gas stream 215 are drawn through the adsorption media 220 and in a second position the coolant gas stream is exhausted to the blower 242 downstream of the adsorption media 220 or simply out the sample intake 227 or another pressure relief port (not depicted).

Figure 3:
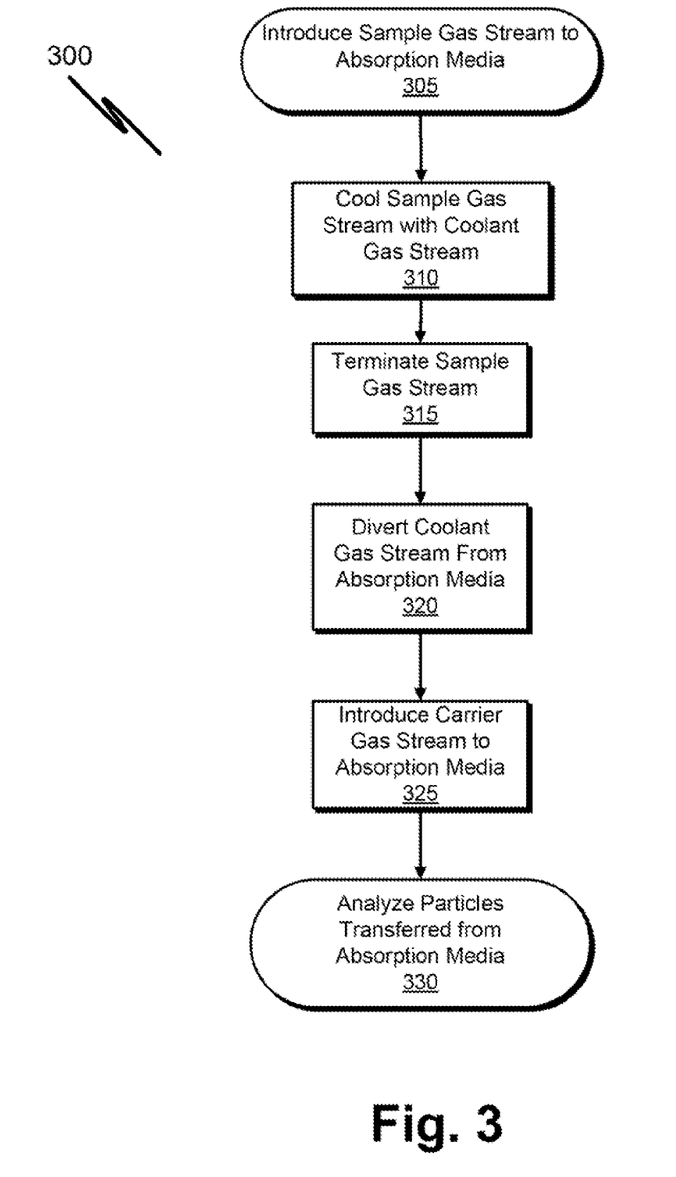

FIG. 3 is a flow diagram illustrating operation of the apparatus 200, in accordance with an embodiment. The method 300 begins at operation 305 with initiated the collection system by energizing the blower 242 which draws the sample gas stream 205 into the second duct 230 and through the adsorption media 220. For example, in one embodiment, the sample gas stream 205 is conducted through the adsorption media 220 in a direction predominantly orthogonal to a longest dimension of the adsorption media 220. During operation 305, LVP particles are adsorbed by the adsorption media 220. With the adsorption media 220 exposed to the sample gas stream 205, the blower 241 is energized at operation 310 to pass the coolant gas stream 215 over the heat transfer surfaces 235 initiating the cold air supply. At operation 310, the sample gas stream 205 is mixed with the coolant gas stream 215 to reduce the temperature of the coolant gas stream 205 and/or the adsorption media 220. With the adsorption media 220 exposed to the cooled sample gas stream and the vapor pressure of the HVP explosives entrained in the sample gas stream 205 reduced and, HVP particles are transferred from the sample gas stream 205 to the adsorption media 220.

Generally, the total duration of both the operations 305 and 310 is between 4 and 8 seconds for the exemplary system employing a $Q_1$ and $Q_2$ that are each at least 50 liters/second and often to be in the range of 100-200 liters/second, depending on the application. In embodiments, the duration of operation 305 may be about 1-2 seconds with the remaining majority of particle collection time spent at operation 310 in cases where both LVP and HVP particles may be adsorbed at the reduced sample stream temperature ($T_4$). Alternatively, the sequence of operations 305 and 310 may be such that the blower 241 is energized before the blower 242 to pre-cool the adsorption media 220.

At operation 315, the collection phase is terminated by denergizing the blower 242 and at operation 320, the coolant gas stream 215 is also diverted from the adsorption media 220, for example by actuating the bypass 265. Alternatively, the blower 241 may be denergized. With the collection phase completed, a desorption cycle is commenced at operation 325 by exposing the adsorption media 220 to the carrier gas stream 255. For example, in one embodiment, the carrier gas stream 255 is conducted across the adsorption media 220 in a direction parallel to a longest dimension of the adsorption media 220. In particular embodiments, operation 325 is commenced after diverting the coolant gas stream 215 at operation 320. The desorbed particles now entrained in the carrier gas stream 255 are then transported to the chemical detector 290 and the LVP and HVP particles transferred from the adsorption media 220 are analyzed at operation 330.

FIG. 4 illustrates a schematic of an apparatus 400 for collecting particles entrained in a sample gas stream. The apparatus 400 incorporates the chiller 210 as well as many other components introduced in reference to apparatus 200. The functional and structural characteristics of the components in apparatus 400 which share a reference number with apparatus 200 are understood to be the same as described in the context of apparatus 200 in absence of any further description in the context of apparatus 400.

The apparatus 400 further includes an adsorption media heater 470 to heat the adsorption media 220 to temperatures greater than a temperature of the carrier gas stream and thermally desorb the particles to the carrier gas stream while the adsorption media is in fluid communication with the third duct. Thermal desorption of the LVP and HVP particles from the adsorption media 220 is controlled in a manner which avoids generating appreciable levels of decomposition products, particularly of the HVP particles. In accordance with one embodiment, adsorption media heater 470 comprises a means to resistively heat the adsorption media 220. One advantageous implementation of such resistive heating is described in detail in U.S. Pat. No. 7,299,711. Other known heating means, such as lamp (radiative) heating, convective heating, inductive heating, etc. may also be implemented in a conventional manner to achieve a similar controlled thermal desorption of the LVP and HVP particles from the adsorption media 220.

Figure 5:
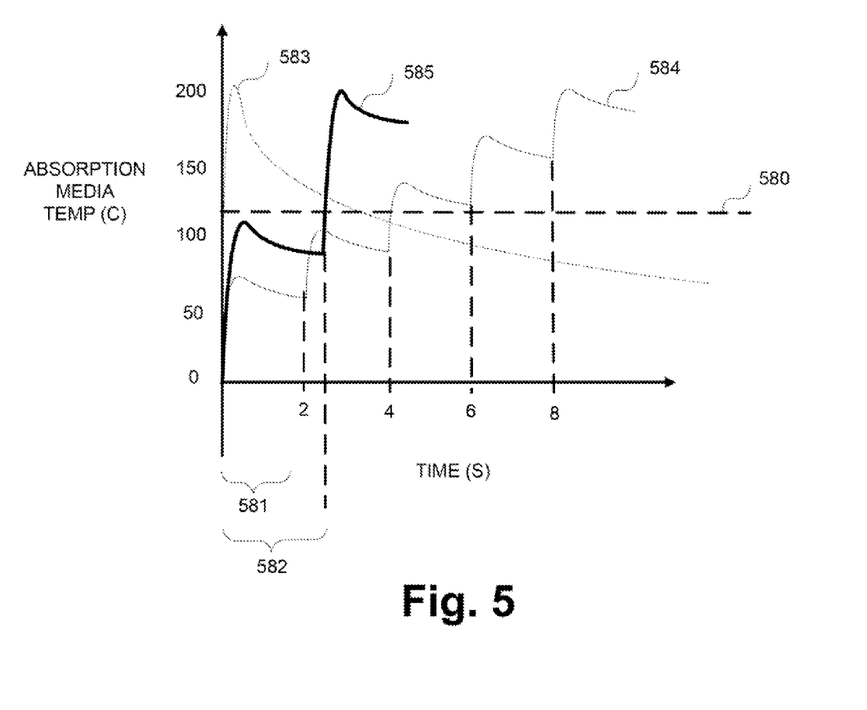

In the exemplary embodiment, the adsorption media heater 470 is controlled, for example by way of the heating power supply 475, by an algorithm implemented in hardware (ASIC, FPGA, etc.) or software to incrementally heat the adsorption media 220 in stages with each heating stage having a predetermined dwell time at a predetermined temperature. FIG. 5 is a graph of adsorption media temperature over time for a staged transfer of HVP and LVP particles into a carrier gas, in accordance with certain embodiments. FIG. 5 is described concurrently with FIG. 6, which is a flow diagram illustrating staged adsorption media heating, in accordance with an embodiment. Operation of the apparatus 400 therefore is to follow the method 300 with the desorption phase (e.g., beginning with operation 325) further including the staged heating operations illustrated in FIG. 6.

Figure 6:
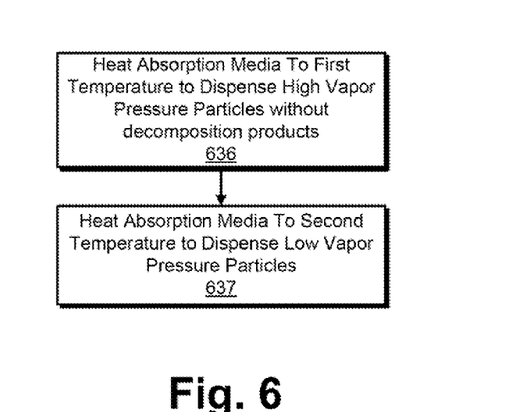

In an embodiment, the adsorption media heater 470 is to heat the adsorption media 220 at operation 636 to a first elevated temperature to desorb a HVP particle during a first dwell time. During operation 636, the adsorption media is held a temperature which is below a threshold temperature at which decomposition products of the HVP particle are generated. Subsequently, at operation 637, the adsorption media heater 470 is to heat the adsorption media 220 to a second elevated temperature to desorb a LVP particle during a second dwell time.

Referring to FIG. 5, the threshold temperature 580 may be predetermined as well as the dwell times 581 and 582 to permit desorption of one or more HVP specie during a first desorption stage. In FIG. 5, time (seconds) is plotted on the x-axis while the temperature of the adsorption media 220 is plotted on the y-axis. Three different heating curves, 584, 585 and 586 are illustrated in FIG. 5. Heating curve 583 represents a flash heating which reaches a maximum elevated adsorption media temperature of about 200° C. nearly instantaneously (approximately 0.3 seconds in certain implementations). The heating curve 584 represents a first controlled heating in which the adsorption media temperature is incremented by approximately 50° C. in each of five distinct stages, each stage having a dwell time 581 of about 2 seconds. The heating curve 585 represents a second controlled heating in which the adsorption media temperature is incremented to just below the threshold 580 in a first stage (e.g., operation 636) and then incremented to the maximum elevated adsorption media temperature in a second stage (e.g., operation 637), with each of stage having a dwell time 582 of 2-3 seconds.

Figure 7:
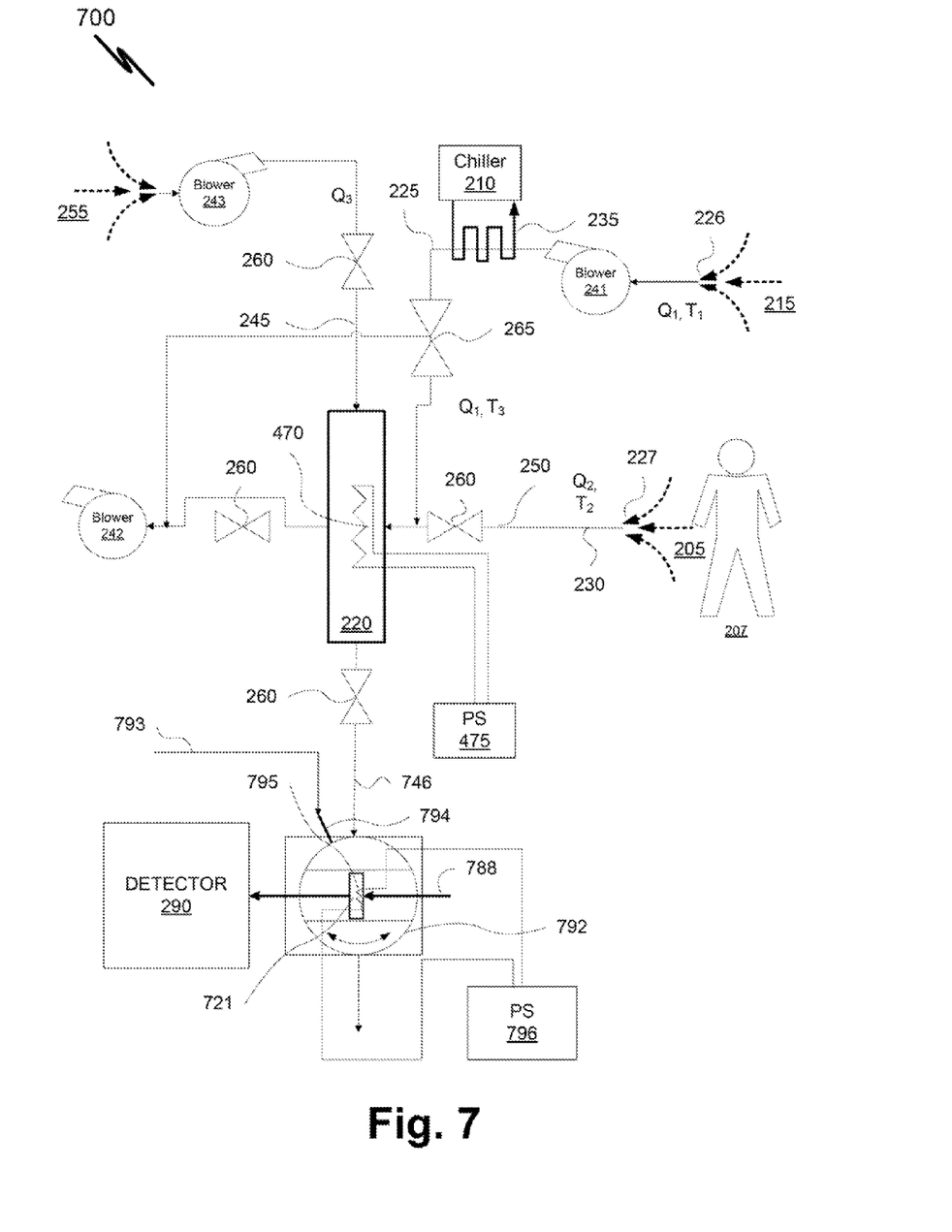

While the heating curve 584 can be expected to generate a significant amount of decomposition products associated the HVP particles. Both staged heating curves 584 and 585 are suitable for reducing the decomposition products associated various HVP particles. The staged heating curve 584 is advantageous where a time divided release of particles into the second carrier gas stream is further useful for improving resolution of the detector 290, for example as described in U.S. Pat. No. 7,299,711. However, such time division of species can reduce overall apparatus throughput and where the adsorption media 220 forms a component of a first preconcentration stage that is followed by a second preconcentration stage (e.g., as depicted in FIG. 7), specie differentiation affected in the first stage may be lost when all species are subsequently collected onto a second adsorption media. As such, the staged heating curve 585 is advantageous for avoiding decomposition of HVP particles while maintaining high system throughput.

FIG. 7 illustrates a schematic of an apparatus 700 for collecting particles entrained in a sample gas stream, the apparatus incorporates a high volume chiller and multi-staged preconcentrators, in accordance with an embodiment. The apparatus 700 incorporates the chiller 210 as well as many other components introduced in reference to apparatus 400. The functional and structural characteristics of the components in apparatus 700 which share a reference number with apparatus 400 are understood to be the same as described in the context of apparatus 400 in absence of any further description in the context of apparatus 700.

In the illustrative embodiment, the apparatus 700 includes a second preconcentration stage employing a second adsorption media 721, downstream of a first preconcentration stage employing the adsorption media 220. Generally the second adsorption media 721 may be any of the embodiments described for adsorption media 220. The two stage preconcentration of the sample gas stream 205 may be implemented in part based on the multi-staged system described in U.S. Pat. No. 6,345,545. As illustrated in FIG. 7, an output stage conducting the carrier gas stream 255 is coupled to an input stage duct 746 which is further coupled to a rotatable valve 792. Rotatable valve 792 is operable to alternately expose the second adsorption media 721 to the carrier gas stream 255 while in a first state and to expose the second adsorption media 721 to a second carrier gas stream 788 while in a second state (depicted).

The second preconcentrator stage further includes a vortex tube 794 through which a second coolant gas flow 793 (e.g., originating from a compressed gas source) is introduced while the rotatable valve 792 is in the first state. The vortex tube 794 thereby serves to reduce the temperature of the carrier gas stream 255 to promote particle adsorption at the second adsorption media 721. As the carrier gas stream 255 has the third volumetric flow rate, $Q_3$, which is substantially smaller than $Q_2$, the cooling capacity of a conventional vortex cooler is sufficient in the second preconcentration stage to reduce the temperature of the carrier gas stream 255 from a temperature elevated by heating of the adsorption media 220 (e.g., 100° C.) during the first desorption phase (e.g., operation 636). For example, in certain embodiments where $Q_1$ is at least 200 liters/second, $Q_3$ is approximately 2 liters/second.

With the rotatable valve 792 in the second state, the second carrier gas stream 788 is conducted at a fourth volumetric flow rate, $Q_4$, to the chemical detector 290, permitting desorption of the LVP and HVP particles collected by the second adsorption media 721. As an example, $Q_4$ may be about 200 mL/minute for an embodiment where $Q_3$ is 2 liters/second. As further illustrated, while the rotatable valve 792 is in the second state, the second adsorption media 721 is heated to an elevated temperature to thermally desorb the LVP and HVP particles collected in the second preconcentrator stage. In one such embodiment, the second adsorption media 721 is controllably heated for time divisioned desorption, for example by controlling the second resistive heater 795 via the second power supply 796 to heating the second adsorption media 721 in the manner illustrated by the heating curve 584 (FIG. 5).

Figure 8:
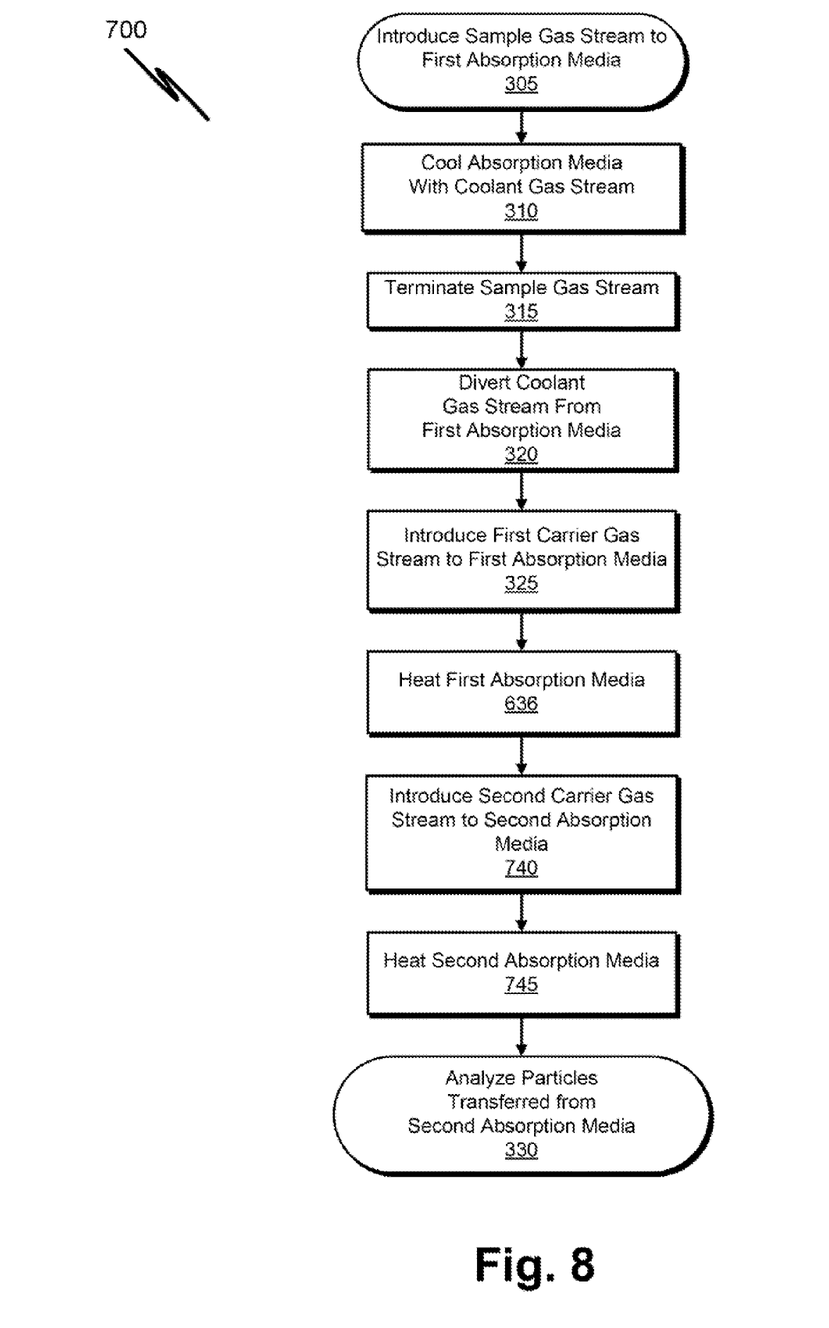

FIG. 8 is a flow diagram illustrating operation of the apparatus depicted in FIG. 7, in accordance with an embodiment. The method 700 begins at operation with 310 with operations 310, 315, 320, 325 and 636 are proceeding as previously described elsewhere herein. At operation 740 the second adsorption media 721 is exposed to the carrier gas stream 255 (and second coolant gas flow 793). After the rotatable valve 792 rotates to the second state at operation 745, the second adsorption media 721 is heated to a third elevated temperature during a second dwell time. The third elevated temperature may be predetermined to thermally desorb a first chemical specie preferentially over a second chemical specie. In a further embodiment the second adsorption media 721 is heated to a fourth predetermined elevated temperature, higher than the third elevated temperature, to thermally desorb the second chemical specie for a time divided release of the particles into the second carrier gas stream 788.

It is to be understood that the above description is intended to be illustrative, and not restrictive. Many other embodiments will be apparent to those of skill in the art upon reading and understanding the above description. Although the present invention has been described with reference to specific exemplary embodiments, it will be recognized that the invention is not limited to the embodiments described, but can be practiced with modification and alteration. Accordingly, the specification and drawings are to be regarded in an illustrative sense rather than a restrictive sense.

What is claimed is:

1. An apparatus for collecting particles entrained in a sample gas stream, comprising:
    a first duct to conduct a coolant gas stream at a first volumetric flow rate;
    a second duct to conduct the sample gas stream at a second volumetric flow rate;
    a chiller coupled to the first duct to cool the coolant gas stream to a temperature below that of the sample gas stream;
    a third duct to conduct a carrier gas stream having a third volumetric flow rate toward a downstream particle detector, the third volumetric flow rate being lower than the second volumetric flow rate; and
    an adsorption media to be in fluid communication with each of the sample gas stream and the coolant gas stream concurrently to collect the particles entrained in the sample gas stream at a temperature below that of the sample gas stream, the adsorption media further to be in alternate fluid communication with the third duct to transfer the particles from the adsorption media to the carrier gas stream.

2. The apparatus of claim 1, wherein the first and second ducts are to conduct the coolant gas stream and sample gas stream in parallel upstream of the adsorption media, with the chiller upstream of a union joining the first and second ducts being upstream or coincident with the adsorption media.

3. The apparatus of claim 1, wherein the first volumetric flow rate is at least equal to the second volumetric flow rate.

4. The apparatus of claim 3, wherein the second volumetric flow rate is at least 50 liters/sec.

5. The apparatus of claim 2, further comprising a bypass upstream of the adsorption media, the bypass operable in a first position to conduct the coolant stream toward the adsorption media when the sample gas stream is in fluid communication with the adsorption media and operable in a second position to isolate the coolant stream from the adsorption media when the carrier gas stream is in fluid communication with the adsorption media.

6. The apparatus of claim 1, further comprising:
    a first impeller to induce the coolant gas stream to pass through the first duct;
    a second impeller to induce the sample gas stream to pass through the second duct and impinge on the adsorption media; and
    a third impeller to induce the carrier gas stream to pass through the third duct and impinge on the adsorption media.

7. The apparatus of claim 1, wherein the chiller comprises an air coil with a refrigerant on a liquid side and the coolant gas on an air side.

8. The apparatus of claim 7, wherein the chiller is operable to cool the coolant gas stream to between 0 and 15° C.

9. The apparatus of claim 1, further comprising a heater to heat the adsorption media to temperature greater than the sample gas stream temperature to a thermally desorb the particles to the carrier gas stream while the adsorption media is in fluid communication with the third duct.

10. The apparatus of claim 9, wherein the adsorption media is to thermally desorb a high vapor pressure particle during a first dwell time at which the adsorption media is held at a first elevated temperature predetermined to be below a threshold temperature at which decomposition products of the high vapor pressure particle are generated, and wherein the adsorption media is to thermally desorb a low vapor pressure particle upon a further heating of the adsorption media to a second elevated temperature, higher than the first elevated temperature.

11. The apparatus of claim 1, further comprising:
    a second adsorption media to be in fluid communication with the carrier gas stream to collect the particles entrained in the carrier gas stream, the adsorption media further to be in alternate fluid communication with a fourth duct to transfer the particles from the second adsorption media to a second carrier gas stream having a fourth volumetric flow rate and moving toward the downstream particle detector, the fourth volumetric flow rate being lower than the third volumetric flow rate.

12. The apparatus of claim 11, wherein the second adsorption media is to be heated to a third elevated temperature during a second dwell time, the third elevated temperature predetermined to thermally desorb a first chemical specie preferentially over a second chemical specie, and wherein the second adsorption media is to be heated to a fourth elevated temperature, higher than the third elevated temperature and predetermined to thermally desorb the second chemical specie for a time divided release of the particles into the second carrier gas stream.

13. An apparatus for collecting particles entrained in a sample gas stream, comprising:
   a first duct to conduct a cold air supply at a first volumetric flow rate,
   a second duct to conduct the sample gas stream at a second volumetric flow rate, wherein the first and second volumetric flows rates are each at least 50 liters/sec;
   a chiller coupled to the first duct to cool the cold air supply to a temperature below that of the sample gas stream wherein the chiller is operable to cool the cold air supply by at least 10° C.; and
   a third duct to conduct a carrier gas stream toward a downstream particle detector; and
   an adsorption media to be in fluid communication with each of the sample gas stream and the cold air supply concurrently to collect the particles entrained in the sample gas stream at a temperature below that of the sample gas stream, the adsorption media further to be in alternate fluid communication with the third duct to transfer the particles from the adsorption media to the carrier gas stream.

14. The apparatus of claim 13, wherein the chiller comprises an air coil with a refrigerant on a liquid side and ambient intake air on an air side.

15. The apparatus of claim 13, further comprising a heater to incrementally elevate the adsorption media temperature while the adsorption media is in fluid communication with the third duct, wherein the heater is to hold the adsorption media at a first elevated temperature for a dwell time of at least 2 seconds, wherein the first elevated temperature is below a threshold temperature at which decomposition products of the high vapor pressure particle are generated.

16. A method for detecting particles entrained in a sample gas stream, the method comprising:
   cooling a coolant gas stream having a first volumetric flow rate;
   mixing the sample gas stream with the coolant gas stream, the sample gas stream having a second volumetric flow rate a temperature above that of the coolant gas stream;
   exposing an adsorption media to the cooled sample gas stream;
   diverting the coolant gas and sample gas streams from the adsorption media;
   conducting a carrier gas stream across the adsorption media toward a downstream particle detector after diverting the coolant gas stream, wherein the carrier gas stream has a third volumetric flow rate lower than the second volumetric flow rate; and
   detecting the particles transferred from the adsorption media to the carrier gas stream.

17. The method of claim 16, wherein the sample gas stream and coolant gas stream are conducted in parallel upstream of the adsorption media.

18. The method of claim 16, wherein the second volumetric flow rate is at least equal to the first volumetric flow rate.

19. The method of claim 18, wherein the first volumetric flow rate is at least 50 liters/sec.

20. The method of claim 16, wherein diverting the coolant gas stream from the adsorption media further comprises:
   bypassing a union joining the second duct to the first duct to isolate the coolant stream from the first duct when the carrier as stream is in fluid communication with the adsorption media.

* * * * *